United States Patent [19]
Kerwin

[11] Patent Number: 6,160,098
[45] Date of Patent: Dec. 12, 2000

[54] METHOD FOR CONTROL OF FUNCTIONALITY DURING CROSS-LINKING OF HEMOGLOBINS

[75] Inventor: Bruce A. Kerwin, Lafayette, Colo.

[73] Assignee: Baxter Biotech Technology Sàrl, Neuchâtel, Switzerland

[21] Appl. No.: 09/077,486

[22] Filed: May 29, 1998

Related U.S. Application Data

[63] Continuation of application No. PCT/US96/18920, Nov. 27, 1996.
[60] Provisional application No. 60/024,760, Nov. 30, 1995, and provisional application No. 60/021,000, Jun. 28, 1996.
[51] Int. Cl.$^7$ ............................................... C07K 14/805
[52] U.S. Cl. .................. 530/385; 530/380; 530/386; 530/405; 530/406; 514/6; 514/2; 514/12; 424/529; 435/69.6
[58] Field of Search ................. 514/6, 2, 12; 424/529; 435/69.6; 530/380, 385, 386, 405, 406

[56] References Cited

U.S. PATENT DOCUMENTS

| | | | |
|---|---|---|---|
| Re. 34,271 | 6/1993 | Walder | 530/385 |
| 4,053,590 | 10/1977 | Bonsen et al. | 424/177 |
| 4,336,248 | 6/1982 | Bonhard et al. | 424/101 |
| 4,343,715 | 8/1982 | Bonaventura et al. | 252/186 |
| 4,401,652 | 8/1983 | Simmonds et al. | 424/101 |
| 4,439,357 | 3/1984 | Bonhard et al. | 260/112 |
| 4,473,494 | 9/1984 | Tye | 260/112 |
| 4,526,715 | 7/1985 | Kothe et al. | 260/112 |
| 4,598,064 | 7/1986 | Walder | 514/6 |
| 4,826,811 | 5/1989 | Sehgal et al. | 514/6 |
| 4,861,867 | 8/1989 | Estep | 530/385 |
| 5,028,588 | 7/1991 | Hoffman et al. | 514/6 |
| 5,084,558 | 1/1992 | Rausch et al. | 530/385 |
| 5,194,590 | 3/1993 | Sehgal et al. | 530/385 |
| 5,239,061 | 8/1993 | Fronticelli et al. | 530/385 |
| 5,296,465 | 3/1994 | Rausch et al. | 514/6 |
| 5,320,965 | 6/1994 | Chiang | 436/11 |

FOREIGN PATENT DOCUMENTS

| | | | |
|---|---|---|---|
| 231236 | 6/1986 | European Pat. Off. | C07K 3/20 |
| 277289 | 11/1987 | European Pat. Off. | A61K 37/14 |
| WO89/12456 | 12/1989 | WIPO | A61K 37/14 |
| WO9013645 | 5/1990 | WIPO | C12N 15/12 |
| WO9116349 | 10/1991 | WIPO | C07K 13/00 |
| WO9211283 | 7/1992 | WIPO | |
| WO9222646 | 12/1992 | WIPO | C12N 15/00 |
| WO9308831 | 5/1993 | WIPO | A61K 37/14 |
| WO9422482 | 10/1994 | WIPO | A61K 47/42 |
| WO9513034 | 5/1995 | WIPO | A61F 5/04 |
| WO9514038 | 5/1995 | WIPO | C07K 14/80 |
| WO9627388 | 9/1996 | WIPO | A61K 38/42 |

OTHER PUBLICATIONS

Rabiner et al.; "Evaluation of a Stroma–Free Hemoglobin Solution for use as a Plasma Expander"; J. Exp. Med. 126:1127–1142 (1967).

Tentori et al., "Hemoglobinometry in Human Blood"; Meth. Enzymol.; 76:707–715 (1981).

Benesch et al.; "Preparation and Properties of Hemoglobin Modified with Derivatives of Pyridoxal"; Meth. Enzymol.; 76:147–159 (1981).

DiIorio; "Preparation of Derivatives of Ferrous and Ferric Hemoglobin"; Meth. Enzymol.; 76:57–72 (1981).

Giardina et al.; "Measurement of Binding of Gaseous and Nongaseous Ligands to Hemoglobins by Conventional Spectrophotometric Procedures"; Meth. Enzymol; 76:417–427 (1981).

Gill; "Measurement of Oxygen Binding by Means of a Thin–Layer Optical Cell"; Meth. Ezymol.; 76:427–438 (1981).

Imai; "Measurement of Accurate Oxygen Equilibrium Curves by an Automatic Oxygenation Apparatus"; Meth. Enzymol.; 76:438–449 (1981).

Geoghegan et al.; "Alternative Reducing Agents for Reductive Methylation of Amino Groups in Proteins"; Int. J. Peptide Protein Res.; 17:345–352 (1981).

Vlahakes et al.; "Hemodynamic Effects and Oxygen Transport Properties of a New Blood Substitute in a Model of Massive Blood Replacement"; J. Thorac. Cardiovas. Surg.; 100:379–388 (1990).

Hoffman et al.; "Expression of Fully Functional Tetrameric Human Hemoglobin in *Escherichia coli*"; Proc. Natl. Acad. Sci. USA; 87:8521–8525 (1990).

Biro et al.; "Studies on Blood Substitutes Based on Hemoglobin and Perfluorocarbon"; Biomat. Art. Cells & Immob. Biotech.; 20:1013–1020 (1992).

Vandegriff; "Blood Substitutes: Engineering the Haemoglobin Molecule"; Biotechnology and Genetic Engineering Rev.; 10:403–453 (1992).

Spahn et al.; "Cardiovascular and Coronary Physiology of Acute Isovolemic Hemodilution: A Review of Nonoxygen–Carrying and Oxygen–Carrying Solutions"; Aneth. Analog.; 78:1000–1021 (1994).

Hargrove et al.; "His$^{64}$(E7)→Tyr Apomyoglobin as a Reagent for Measuring Rates of Hemin Dissociation"; J. Biol. Chem..; 269:4207–4214 (1994).

Barnikol; "Influence of the Polymerization Step Alone on Oxygen Affinity and Cooperativity During Production of Hyperpolymers from Native Hemoglobins with Crosslinkers"; Art. Cells, Blood Substitutes, and Immobilization Biotechnology; 22:725–731 (1994).

*Primary Examiner*—E. T. Moezie
*Attorney, Agent, or Firm*—Senniger, Powers, Leavitt & Roedel

[57] ABSTRACT

The present invention relates to cross-linked hemoglobins, and particularly to methods of controlling the functionality of such hemoglobins. The controlled functionalities include the $P_{50}$ and the Hill coefficient. The present invention provides methods for producing a cross-linked hemoglobin with specific final functionalities by regulating the amount of both total hemoglobin and R-state hemoglobin prior to cross-linking, and by modulating cross-linking reaction conditions such as time, temperature, pH and the ratio of cross-linking reagent to hemoglobin.

21 Claims, No Drawings

METHOD FOR CONTROL OF FUNCTIONALITY DURING CROSS-LINKING OF HEMOGLOBINS

REFERENCE TO RELATED APPLICATIONS

This application is a continuation-in-part of U.S. Provisional application Ser. No. 60/024,760, filed Nov. 20, 1995, now abandoned, and a continuation-in-part of U.S. Provisional application Ser. No. 60/021,000filed Jun. 28, 1996, now abandoned.

TECHNICAL FIELD

This invention relates to crosslinked hemoglobins, and particularly to methods of controlling the functionality of such hemoglobins.

BACKGROUND OF THE INVENTION

The oxygen carrying portion of red blood cells is the protein hemoglobin. Hemoglobin is a tetrameric molecule composed of two identical alpha globin subunits ($\alpha_1$, $\alpha_2$), two identical beta globin subunits ($\beta_1$, $\beta_2$) and four heme molecules, with one heme incorporated per globin. Heme is a large macrocyclic organic molecule containing an iron atom; each heme can combine reversibly with one ligand molecule such as oxygen. In a hemoglobin tetramer, each alpha subunit is associated with a beta subunit to form a stable alpha/beta dimer, two of which in turn associate to form the tetramer. The subunits are noncovalently associated through Van der Waals forces, hydrogen bonds and salt bridges.

Severe blood loss often requires replacement of the volume of lost blood as well as the oxygen carrying capacity of that blood. This replacement is typically accomplished by transfusing red blood cells (RBC's), either as packed RBC's or as units of whole blood. However, it is not always possible, practical or desirable to transfuse a patient with donated blood. Human blood transfusions are associated with many risks such as, for example, transmission of diseases and disease causing agents such as human immunodeficiency virus (HIV), hepatitis, Yersinia enterocolitica, cytomegalovirus, and human T-cell leukemia virus. In addition, blood transfusions can be associated with immunologic reactions such as hemolytic transfusion reactions, immunosuppresion, and graft versus host reactions. Moreover, blood must be typed and cross-matched prior to administration, and may not be available due to limited supplies.

When human blood is not available or the risk of transfusion is too great, plasma expanders can be administered. However, plasma expanders, such as colloid and crystalloid solutions, replace only blood volume, and not oxygen carrying capacity. In situations where blood is not available for transfusion, a red blood cell substitute that can transport oxygen in addition to providing volume replacement is desirable. Solutions of cell-free hemoglobin can increase and/or maintain plasma volume and decrease blood viscosity in the same manner as conventional plasma expanders, but, in addition, a hemoglobin-based red blood cell substitute can support adequate transport of oxygen from the lungs to peripheral tissues. Moreover, an oxygen-transporting hemoglobin-based solution can be used in most situations where red blood cells are currently utilized. For example, oxygen-transporting hemoglobin-based solutions can be used to temporarily augment oxygen delivery during or after pre-donation of autologous blood prior to the return of the autologous blood to the patient.

To address this need, a number of red blood cell substitutes have been developed (Winslow, R. M.(1992) *Hemoglobin-based Red Cell Substitutes,* The Johns Hopkins University Press, Baltimore 242 pp). These substitutes include synthetic perfluorocarbon solutions, (Long, D. M. European Patent 0307087), stroma-free hemoglobin solutions, both chemically crosslinked and uncrosslinked, derived from a variety of mammalian red blood cells (Rausch, C. and Feola, M., U.S. Pat. Nos. 5,084,558 and 5,296,465; Sehgal, L. R., U.S. Pat. Bos. 4,826,811 and 5,194,590; Vlahakes, G J. et al., (1990) *J. Thorac. Cardiovas. Surg.* 100: 379–388) and hemoglobins expressed in and purified from genetically engineered organisms (for example, non-erythrocyte cells such as bacteria and yeast, Hoffman et al., WO 90/13645; bacteria, Fronticelli, C. et al., U.S. Pat. No. 5,239,061; yeast, De Angelo et al., WO 93/08831 and WO 91/16349; and transgenic mammals, Logan et al., WO 92/22646; Townes, T. M and McCune, S. L., WO 92/11283). These red blood cell substitutes have been designed to replace or augment the volume and the oxygen carrying capability of red blood cells.

However, red blood cell replacement solutions that have been administered to animals and humans have exhibited certain adverse events upon administration. These adverse reactions have included hypertension, renal failure, neurotoxicity, and liver toxicity (Winslow, R. M., (1992) *Hemoglobin-based Red Cell Substitutes,* The Johns Hopkins University Press, Baltimore 242 pp.; Biro, G. P. et al., (1992) *Biomat., Art. Cells & Immob. Biotech.* 20: 1013–1020). In the case of perfluorocarbons, hypertension, activation of the reticulo-endothelial system, and complement activation have been observed (Reichelt, H. et al., (1992) in *Blood Substitutes and Oxygen Carriers,* T. M. Chang (ed.), pg. 769–772; Bentley, P. K. supra, pp. 778–781). For hemoglobin based oxygen carriers, renal failure and renal toxicity is the result of the formation of hemoglobin $\alpha/\beta$ dimers. The formation of dimers can be prevented by chemically crosslinking (Sehgal, et al., U.S. Pat. Nos. 4,826,811 and 5,194,590; Walder, J. A. U.S. Reissue Pat. No. RE34271) or genetically linking (Hoffman, et al., WO 90/13645) the hemoglobin dimers so that the tetramer is prevented from dissociating.

Prevention of dimer formation has not alleviated all of the adverse events associated with hemoglobin administration. Blood pressure changes and gastrointestinal effects upon administration of hemoglobin solutions have been attributed to vasoconstriction resulting from the binding of endothelium derived relaxing factor (EDRF) by hemoglobin (Spahn, D. R. et al., (1994) *Anesth. Analg.* 78: 1000–1021; Biro, G. P., (1992) *Biomat., Art. Cells & Immob. Biotech.,* 20: 1013–1020; Vandegriff, K. D. (1992) *Biotechnology and Genetic Engineering Reviews,* Volume 10: 404–453 M. P. Tombs, Editor, Intercept Ltd., Andover, England). Endothelium derived relaxing factor has been identified as nitric oxide (NO) (Moncada, S. et al., (1991) *Pharmacol. Rev.* 43: 109–142 for review); both inducible and constitutive NO are primarily produced in the endothelium of the vasculature and act as local modulators of vascular tone.

When hemoglobin is contained in red blood cells, it cannot move beyond the boundaries of blood vessels. Therefore, nitric oxide must diffuse to the hemoglobin in an RBC before it is bound. When hemoglobin is not contained within an RBC, such as is the case with hemoglobin-based blood substitutes, it may pass beyond the endothelium lining the blood vessels and penetrate to the extravascular space (extravasation). Thus, a possible mechanism causing adverse events associated with administration of extracellular hemoglobin may be excessive inactivation of nitric oxide due to hemoglobin extravasation. Furthermore, NO is constitutively synthesized by the vascular endothelium. Inactivation of NO in the endothelium and extravascular space may lead to vasoconstriction and the pressor response as well as other side effects observed after infusions of cell-free hemoglobin. Larger hemoglobins may serve to reduce hypertension associated with the use of some extracellular hemoglobin solutions.

In addition, the half-life of these molecules is limited and is much lower than hemoglobin that is contained within red blood cells. Such short-lived hemoglobin is accordingly rapidly cleared from the body and may not be appropriate for oxygen delivery over longer periods of time, from hours to days. Hemoglobin that is intramolecularly and/or intermolecularly crosslinked by a chemical crosslinker may have an increased half-life. The increased half-life may be due to the inhibition of hemoglobin clearance mechanisms by the presence of the crosslinker in the three-dimensional structure of the hemoglobin. Such chemical crosslinkers may interfere with clearance processes such as haptoglobin binding or binding to other specific hemoglobin receptors.

As discussed above, hemoglobin from any source can be chemically crosslinked using a variety of chemistries. Aldehydes such as glutaraldehyde and glycolaldehyde have been used to crosslink hemoglobin both intramolecularly (within a tetramer) and intermolecularly (between tetramers). Intramolecular crosslinks serve to prevent dimerization into alpha/beta dimers and may also alter oxygen affinity and cooperativity, while intermolecular crosslinks create polymers of tetrameric hemoglobin. Polymeric hemoglobins may result in reduced extravasation because of their increased size. Reduced extravasation may, in turn, lead to reduced pressor effects resulting from infused hemoglobin solutions.

One hemoglobin tetramer binds four oxygen molecules. Because hemoglobin is a cooperative molecule, the binding of one oxygen molecule at one heme increases the ease with which the next oxygen molecule is bound. The combination of oxygen affinity and cooperativity of the hemoglobin molecule determines the ease with which the molecule binds and releases oxygen. Both contribute to the shape of the oxygen equilibrium binding curve, which in turn controls the binding of oxygen to hemoglobin in the lungs and the release of oxygen from hemoglobin in the tissues (Bunn and Forget, Hemoglobin: *Molecular, Genetic and Clinical Aspects,* (1986) W. B. Saunders, Philadelphia, Pa., pp 37–60). Therefore, either or both of these functionalities of the hemoglobin molecule can be adjusted to yield a hemoglobin that has suitable parameters for a given application. It is generally thought that an effective blood substitute should have moderately low oxygen affinity and should exhibit some level of cooperative binding of oxygen. Lower oxygen affinities and some preservation of cooperativity can be achieved if the hemoglobin is modified with chemicals designed to reduce oxygen affinity such as pyridoxal-5'-phosphate and related compounds (Snyder and Walder in *Biotechnology of Blood,* J. Goldstein, editor, Butterworth-Heinemann, Boston, (1991) 101–116; Benesch and Benesch (1981), *Meth. Enzymol.* 76: 147–159), or the hemoglobin is very low oxygen affinity prior to crosslinking (e.g. bovine hemoglobin). Treatment of hemoglobin with additional reagents is cumbersome and increases the cost of the product by increasing the material costs and increasing the number of production and purification steps. Cooperativity of the molecule is often significantly reduced during chemical treatments, and is difficult to maintain at levels found in the molecule prior to chemical treatment. Generally, it is desirable to produce a hemoglobin-based blood substitute with more cooperativity rather than less cooperativity.

For use in physiological applications, the hemoglobin should be intramolecularly crosslinked to avoid dimerization and concommittant renal toxicity. Crosslinking of hemoglobin with polyfunctional crosslinkers has been previously described (Bonsen et al., U.S. Pat. No. 4,053,590; Bonhard and Boysen, U.S. Pat. No. 4,336,248; Sehgal et al., U.S. Pat. No. 4,826,811; Hsia, U.S. Pat. No. 5,364,932, see Vandegriff, K. D.(1992) *Biotechnology and Genetic Engineering Reviews,* Volume 10: 404–453 M. P. Tombs, Editor, Intercept Ltd., Andover, England, and Winslow, R. M.(1992) *Hemoglobin-based Red Cell Substitutes,* The Johns Hopkins University Press, Baltimore 242 pp for reviews). However, crosslinking of the hemoglobin in these cases generally yields hemoglobins with higher oxygen affinity (lowered $P_{50}$) and significantly reduced cooperativity (lower n or $n_{max}$) than the hemoglobin that was used as starting material. Chemical crosslinking of hemoglobin, as practiced to date, provides a system to create stabilized tetramers or high molecular weight hemoglobins. However, it is not possible, using existing technologies, to reduce the significant loss of cooperativity of the hemoglobin molecule during chemical crosslinking. Thus, a need exists for methods of controlling loss of cooperativity of intra- or intermolecularly chemically crosslinked hemoglobins by methods that do not require the use of additional chemicals, for example, by regulating deoxygenation or protein concentration of the non-polymerized hemoglobin. The present invention satisfies this need and provides related advantages.

SUMMARY OF THE INVENTION

This invention relates to methods for preparing crosslinked hemoglobin having target functionalities. In one embodiment of the instant invention, the desired functionality is $P_{50}$, that is the desired functionality is the oxygen tension for which a hemoglobin solution is half saturated with oxygen. In another embodiment, the desired functionality is the Hill coefficient. The Hill coefficient is a measure of the cooperativity of the hemoglobin molecule.

The method by which the $P_{50}$ is controlled is accomplished by:

(a) determining initial concentrations of R-state hemoglobin and total hemoglobin in an untreated hemoglobin solution;

(b) comparing the initial concentrations of R-state hemoglobin and total hemoglobin to target concentrations of R-state hemoglobin and total hemoglobin;

(c) if necessary, adjusting the initial concentrations of R state hemoglobin and total hemoglobin to the target concentrations of R-state hemoglobin and total hemoglobin to obtain an adjusted hemoglobin solution; and (d) chemically treating the untreated hemoglobin solution or the adjusted hemoglobin solutions to obtain crosslinked hemoglobin having a target functionality.

The method by which cooperativity (as measured by the Hill coefficient) is controlled is by modulating at least one "Hill coefficient-affecting paramter" such as the time, temperature, pH, rate of addition of hemoglobin, or molar ratio of the crosslinking reagent to hemoglobin during the crosslinking reaction. The starting hemoglobin is partially, and preferentially fully, deoxygenated prior to crosslinking. The target Hill coefficient is in the range from about 1.0 to 3.0, preferably greater than about 1.7, most preferably about 2.2. The time of treatment is preferably up to about 120 minutes, more preferably less than about 10 minutes, most preferably less than about 1 minute. The pH is preferably in the range from about 6.5 to about 7.5. The molar ratio of crosslinking reagent to hemoglobin is preferentially in the range from about 8:1 to about 12.5:1. The hemoglobin and crosslinkining reagent can be added to the crosslinking reaction simultaneously or sequentially.

The crosslinked hemoglobins prepared by the methods of the present invention are intramolecularly crosslinked, or are both intramolecularly and intermolecularly crosslinked. Methods for crosslinking can be achieved by the use of hetero- or homo-polyfunctional crosslinkers, including, for example, bis-imidoesters, bis-succinimidyl esters and aldehydes. Particularly suitable aldehydes are glycolaldehyde or glutaraldehyde. Such crosslinked hemoglobins an also be pyridoxylated or, preferably, non-pyridoxylated. A further aspect of the present invention is recombinant, mutant hemoglobin that is crosslinked. Such recombinant hemoglobins can be, for example, hemoglobin Presbyterian, or rHb1.1, as described below.

DETAILED DESCRIPTION OF THE INVENTION

This invention relates to methods for preparing crosslinked hemoglobin having target functionalities. Hemoglobin functionality is defined by the oxygen affinity ($P_{50}$) and/or the cooperativity (Hill coefficient—either n or $n_{max}$) of the hemoglobin. Both or either of these functionalities can be altered using the methods of the instant invention. By regulating the kind and amount of untreated hemoglobin, a crosslinked hemoglobin with a targeted $P_{50}$, Hill coefficient, or both can be achieved. The cooperativity of the starting material can be adjusted or preserved by regulating the time, temperature and protein concentration of the reaction during the crosslinking.

According to one embodiment of the instant invention, the $P_{50}$ of an untreated hemoglobin solution can be controlled by adjusting the amount of R-state hemoglobin, particularly oxyhemoglobin, in the untreated hemoglobin solution prior to crosslinking. R-state hemoglobin ("relaxed") is the high affinity state of hemoglobin and is the dominant form of hemoglobin when a ligand is bound at the heme pocket. Such ligands include oxygen, carbon monoxide and nitric oxide. When oxygen is bound at the heme, the R-state hemoglobin is denoted oxyhemoglobin. On the other hand, T-state hemoglobin ("tense") is the low affinity state of hemoglobin and is the dominant form of hemoglobin when it is deoxygenated. T-state hemoglobin is also known as deoxyhemoglobin or simply deoxy. Each hemoglobin tetramer in hemoglobin solutions is generally either in the R-state or the T-state, but the hemoglobin solution can contain some tetramers that are in the R-state and others that are in the T-state.

When the amount of R-state hemoglobin solution is decreased in a solution, there is a concommittant rise in the amount of T-state hemoglobin. This is because, in general, in any given hemoglobin solution the sum of the R-state hemoglobin concentration and the T-state hemoglobin concentration is equal to the total hemoglobin concentration. Likewise, the sum of the percentage of R-state hemoglobin in a given solution and the percentage of T-state hemoglobin in a solution is equal to 100% of the hemoglobin in that solution. Thus, according to the methods of the instant invention, a target R-state hemoglobin level is a target R-state hemoglobin concentration or percentage, and because the amount of R-state hemoglobin controls the amount of T-state hemoglobin, a target R-state hemoglobin is by definition a target T-state hemoglobin level. Therefore, a given percentage of hemoglobin molecules in either the R-state or the T-state can be achieved through the techniques used to prepare the untreated hemoglobin solutions, or can be achieved by, for example, adding oxygen scavengers (such as, for example dithionite) or by changing or removing the gas ligand at the heme. The latter method can be accomplished by oxygenation or deoxygenation of the hemoglobin solution to yield a target percentage or concentration of R-state hemoglobin prior to crosslinking, which, in combination with the total hemoglobin concentration, then allows the achievement of a target $P_{50}$.

According to one embodiment of the instant invention, the final target $P_{50}$ of the crosslinked hemoglobin can be controlled by modulating the initial concentration of total hemoglobin and the initial concentration of R-state hemoglobin (Table 1):

TABLE 1

|  | Low R-state Hemoglobin | High R-state Hemoglobin |
| --- | --- | --- |
| Low Total Hemoglobin | Higher final $P_{50}$ Lower final $n_{max}$ | Lower final $P_{50}$ Lower final $n_{max}$ |
| High Total Hemoglobin | Lower final $P_{50}$ Higher final $n_{max}$ | Higher final $P_{50}$ Higher final $n_{max}$ |

The total hemoglobin is the total amount of the hemoglobin protein in the solution, regardless of oxidation state, ligand, or hemoglobin species. Thus the total hemoglobin concentration is the sum of all the hemoglobin species in a solution, and can include methemoglobin, oxyhemoglobin, carbonmonoxyhemoglobin, deoxyhemoglobin and the like. The untreated hemoglobin solution can be prepared so that it is at an appropriate total hemoglobin concentration, in conjunction with the R-state hemoglobin concentration to yield the target final $P_{50}$. Alternatively, the total hemoglobin concentration can be adjusted up or down by concentration and dilution methods known in the art. The total hemoglobin concentration can be measured by any means known in the art. Such means include, for example, determination of absorbance at 280 nm, the biuret assay (Ohnishi, S. T. and Barr, J. K. (1978) *Anal. Biochem.* 86, 193–200), the Lowry assay (Lowry, O. H., Rosebrough, N. J., Farr, A. L. and Randall, R. J. (1951) *J. Biol. Chem.* 193: 265–275) and the bicinchonicic acid method (Smith, P. K., Krohn, R. I., Hermanson, G. T., Mallia, A. K., Gartner, F. H., Provenzano, M. D., Fujimoto, E. K., Goeke, N. M., Olson, B J. and Klenk, D. C. (1985) *Anal. Biochem.* 150, 76–85). A particularly useful method for the determination of total hemoglobin concentration is the conversion of all the hemoglobin in a sample aliquot of a hemoglobin solution to cyanomethemoglobin by addition of an excess potassium ferricyanide with respect to heme, followed by measurement of the cyanomethemoglobin in a suitably equipped spectrophotometer (Tentori, L. and A. M. Salvati, (1981) *Meth. Enzymol.* 76: 707–714).

It will be appreciated that the appropriate set of concentration conditions will depend on the oxygen affinity of the untreated hemoglobin, as well as the target $P_{50}$. The appropriate set of conditions can be readily determined by those skilled in the art. According to the instant invention, there is no need to add any exogenous reagents to the untreated hemoglobin to achieve a desired $P_{50}$ of the final crosslinked hemoglobin, although exogenous reagents can be added to aid in achieving the desired final R-state hemoglobin concentration. For example, at high R-state hemoglobin concentrations, the $P_{50}$ is decreased relative to using untreated hemoglobin with lower concentrations of R-state hemoglobin at the same total hemoglobin concentration. Appropriate combinations of R-state hemoglobin and total hemoglobin to yield a specific target $P_{50}$ can be readily determined by those skilled in the art, using the guidance set forth herein. Note that the specific target $P_{50}$ can be a $P_{50}$ that is the same or different from the $P_{50}$ of the starting material.

In another aspect of the invention, a target cooperativity, which can be measured using the Hill coefficient, can also be achieved by regulating the R-state hemoglobin and total hemoglobin amount, in the same fashion as described above. The cooperativity can be also be affected by varying the R-state hemoglobin amount and the ratio of crosslinking agent to the total hemoglobin concentration. Accordingly, high crosslinking agent to total hemoglobin ratios in the presence of low levels of R-state hemoglobin can result in low cooperativities, while low ratios of crosslinking agent to total hemoglobin in the presence of low levels of R-state hemoglobin can result in increased cooperativity.

Therefore, according to the methods of the instant invention, a given cooperativity can be achieved by adjusting, if necessary, both the total hemoglobin concentration and the R-state hemoglobin concentration (Table 1). In this embodiment, as the concentration of hemoglobin is increased prior to crosslinking, the cooperativity increases relative to using a more dilute untreated hemoglobin solutions at a given amount of R-state hemoglobin. Likewise, at high R-state hemoglobin concentrations, the cooperativity is decreased relative to using untreated hemoglobin with lower concentrations of R-state hemoglobin at the same total hemoglobin concentration. Appropriate conditions can be readily determined by those skilled in the art.

According to another embodiment of the instant invention, the cooperativity of the hemoglobin solution obtained after crosslinking can be significantly preserved by modulating the time, temperature, pH, and molar ratio of crosslinking reagent to hemoglobin in the crosslinking reaction. According to the methods described herein, the $P_{50}$ can be maintained close to the starting value of the untreated hemoglobin, or varied, if desired.

It will be appreciated that an appropriate set of conditions for preservation of cooperativity can be readily determined by those skilled in the art using the guidance provided herein. As mentioned above, the final cooperativity of the crosslinked hemoglobin, whatever the desired molecular weight distribution, can be preserved by modulating the temperature of the reaction, the time of the reaction, the pH of the reaction, and the protein concentration, without significantly affecting the $P_{50}$ of the final solution when all the reactants are mixed simultaneously. A higher final $n_{max}$, relative to the $n_{max}$ of the starting material, (i.e., a smaller decrease in $n_{max}$) can be achieved by (1) performing the reaction at pH's between approximately 6.5–7.5; (2) using a high protein concentration, preferably, greater than 150 mg/m o hemoglobin; and (3) using the guidance in table 2 to set the time and temperature parameters.

TABLE 2

|  | Low Temperature (<10° C.) | High Temperature (>10° C.) |
|---|---|---|
| Long Reaction Times (>10 min) | Lower final $n_{max}$ | Intermediate final $n_{max}$ |
| Short Reaction Times (<10 min) | Intermediate final $n_{max}$ | Higher final $n_{max}$ |

For example, if the reactants, that is the crosslinking agent and the hemoglobin, are mixed simultaneously, conditions that would generally result in the greatest preservation of the cooperativity of the hemoglobin would be a high protein concentration, for example >150 mg/ml, a pH of approximately 7, and a reaction time which gets shorter with higher temperatures (e.g. 1–3 minutes at 25° C. or 10 minutes at 4° C.). Under these conditions, the concentration of salt in the reaction solution has no apparent effect on the cooperativity of the crosslinked hemoglobin product.

If the reactants are not added simultaneously, then the rate of the addition and the mixing protocol of the reactants can affect the cooperativity of the crosslinked hemoglobin product. For example, compared to reactions that are performed by the simultaneous addition of reagents, reactions that are performed by the addition of either the crosslinking agent or the hemoglobin over a period of time can attain higher cooperativities.

For the purposes of the present invention, hemoglobin contained in the untreated hemoglobin solution can be derived from natural, synthetic or recombinant sources. For example, slaughter houses produce very large quantities of hemoglobin-containing blood. Particular species or breeds of animals which produce a hemoglobin especially suitable for a particular use can be specifically bred in order to supply hemoglobin. Transgenic animals can be produced that express non-endogenous hemoglobin as described in Logan, J. S. et al., PCT publication WO 92/22646. Human hemoglobin can be collected from outdated human blood that must be discarded after a certain expiration date.

In addition to extraction from animal or human sources, the genes encoding subunits of a desired naturally occurring or mutant hemoglobin can be cloned, placed in a suitable expression vector and inserted into an organism, such as a microorganism, animal or plant, or into cultured animal or plant cells or tissues. These organisms can be produced using conventional recombinant DNA techniques and the hemoglobin produced by these organisms can then be expressed and collected as described, for example, in Hoffman, S. J and Nagai, K. in U.S. Pat. No. 5,028,588 and Hoffman, et al., WO 90/13645, both herein incorporated by reference. A particularly useful hemoglobin is mutant recombinant hemoglobin, especially a mutant recombinant hemoglobin containing the Presbyterian mutation ($Asn^{108} \rightarrow Lys$).

The untreated hemoglobin solutions can contain crude or purified hemoglobins. Purification of hemoglobin from any source can be accomplished using purification techniques which are known in the art. For example, hemoglobin can be isolated and purified from outdated human red blood cells by hemolysis of erythrocytes followed by chromatography (Bonhard, K., et al., U.S. Pat. No. 4,439,357; Tayot, J. L. et al., EP Publication 0 132 178; Hsia, J. C., EP Patent 0 231 236 B1), filtration (Rabiner, S. F. (1967) et al., *J. Exp. Med.* 126: 1127–1142; Kothe, N. and Eichentopf, B. U.S. Pat. No. 4,562,715), heating (Estep, T. N., PCT publication WO 89/12456, Estep, T. N., U.S. Pat. No. 4,861,867), precipitation (Simmonds, R. S and Owen, W. P., U.S. Pat. No. 4,401,652; Tye, R. W., U.S. Pat. No. 4,473,494) or combinations of these techniques (Rausch, C. W. and Feola, M., EP 0 277 289 B1). Recombinant hemoglobins produced in transgenic animals have been purified by chromatofocusing (Townes, T. M. and McCune, PCT publication WO 92/11283), while those produced in yeast and bacteria have been purified by ion exchange chromatography (Hoffman, S J and Nagai, K. in U.S. Pat. No. 5,028,588 and Hoffman, et al., WO 90/13645, both herein incorporated by reference).

The untreated hemoglobin solution is deoxygenated prior to crosslinking. Hemoglobin solutions can be deoxygenated by any means known in the art. For an example listing of methods see *Chemical Engineering Handbook,* 5th edition, McGraw-Hill, New York (1973) chapter 18. These methods include, for example, addition of oxygen scavengers (such as, for example, dithionite) or removal of the gas ligand at the heme. Deoxygenation of hemoglobin solutions that can be accomplished by liquid-liquid contacting techniques, in which two immiscible liquids are mixed together, one of which contains no dissolved oxygen, but in which oxygen readily dissolves. After the second liquid has absorbed the oxygen, the liquids can be separated by gravity or in a centrifuge. Alternatively, oxygen can be removed by sorption, in which solid particles with a large internal surface area that adsorb dissolved oxygen, for example molecular sieves, are added to a solution. After sorption, the solid particles can be separated from the solution with a centrifuge or filter.

Hemoglobin solutions can be deoxygenated by treatment with an inert gas such as nitrogen or argon. This can be accomplished using gas-liquid contacting techniques wherein oxygen is transported from a solution to a non-oxygen gas phase. Some options for gas-liquid contacting include, for example: (1) packed columns, in which the non-oxygen gas passes upward while a solution trickles downward through a bed of packing; (2) plate columns, similar to packed columns except that they contain a series of horizontal plates that catch the solution; (3) wetted-wall columns in which a solution falls as a film down a bank of vertical tubes; (4) gas transfer membranes, wherein oxygen is transported across a thin membrane that retains liquid on one side and a non-oxygen gas on the other side; (5) gas-sparged tanks, in which non-oxygen gas bubbles through a tank containing the solution; (6) cyclic pressurization, in which a vessel containing the solution is cyclically pressurized with a non-oxygen gas then vented to release the gas and induce bubbles to form in the solution; and (7) liquid atomization, in which the solution is sprayed into a chamber containing a non-oxygen gas.

Of these techniques, a particularly useful technique is packed column deoxygenation, where the solution is deoxygenated by flowing a hemoglobin solution over the column while flowing an inert gas countercurrent to the flow of the hemoglobin solution. The inert gas is any gas that does not bind at the heme group of a hemoglobin molecule, for example argon or nitrogen. An alternative suitable technique for deoxygenation is repeated evacuation of the solution and subsequent or concommittant flushing or sweeping the hemoglobin solution with an inert gas, such as argon or nitrogen (Dilorio, E. E.(1981) in *Methods in Enzymology, Hemoglobins,* 76: 57–71). According to the methods of the instant invention, "deoxygenated" means removal of the majority of the oxygen, preferably at least 90%, most preferably removal of at least 97% of the oxygen.

Both $P_{50}$ and the Hill coefficient can be measured by any means known in the art. Such means include, for example, the determination of an oxygen equilibrium curve. Oxygen equilibrium curves can be collected using any method suitable for such collection. Such means for determination of oxygen equilibrium curves include, for example, the determination of an oxygen equilibrium curve using spectrophotometric techniques (Giardina and Amiconi (1981) *Meth. Enzymol.* 76: 417–427) thin layer optical cell techniques (Gill, (1981) *Meth. Enzymol.* 76: 427–438; Imai (1981) *Meth. Enzymol.* 76: 438–470), and other techniques, such as HEMOX analysis (Hoffman, S. J., Looker, D. L., Roehrich, J. M., Cozart, P. E., Durfee, S. L., Tedesco, J. L. and Stetler, G. L. (1990) *Proc. Natl. Acad. Sci. USA* 87:8521–8525). Hill coefficient calculation is also described by these workers. A particularly suitable technique is the HEMOX analysis technique which can be used to generate an oxygen equilibrium curve for the determination of the $P_{50}$ and Hill coefficient (Hoffman, S. J., Looker, D. L., Roehrich, J. M., Cozart, P. E., Durfee, S. L., Tedesco, J. L. and Stetler, G. L. (1990) *Proc. Natl. Acad. Sci. USA* 87:8521–8525).

According to the methods of the instant invention, once any necessary adjustments of the amounts of R-state hemoglobin and total hemoglobin are performed or adjustments are made in the reaction conditions affecting cooperativity, the hemoglobin is crosslinked using the guidance outlined above with respect to reagent additions. Crosslinking of the hemoglobin can be intramolecular, intermolecular or both intramolecular and intermolecular. Intramolecular crosslinking is crosslinking that is confined to a hemoglobin tetramer, while intermolecular crosslinking is crosslinking that occurs between two or more tetramers. Accordingly, crosslinked hemoglobin is hemoglobin that is crosslinked intramolecularly, intermolecularly or both intramolecularly and intermolecularly. Crosslinking can be accomplished using any reagent suitable for producing a crosslinked hemoglobin, such as those linkers discussed in Wang, S. S. (1993) Chemistry of Protein Conjugation and Cross-linking. CRC Press. Other suitable crosslinking methods are described, for example in Vandegriff, K. D.(1992) *Biotechnology and Genetic Engineering Reviews,* Volume 10: 404–453 M. P. Tombs, Editor, Intercept Ltd., Andover, England; and Winslow, R. M.(1992) *Hemoglobin-based Red Cell Substitutes,* The Johns Hopkins University Press, Baltimore 242 pp. Such crosslinking chemistries are generally linkers containing one or more functional groups. These functional groups can be the same or different (i.e., homo-bifunctional linkers, heterobifunctional linkers, homopolyfunctional linkers, or heteropolyfunctional linkers) and include, for example, bis-imidoesters, bis-succinimidyl esters and dialdehyde and polyaldehyde crosslinkers, such as glycolaldehyde, glutaraldehyde and oxidized ring structures of sugars or nucleotides. A particularly suitable chemistry is homopolyfunctional crosslinking, such as aldehyde crosslinking, particularly glutaraldehyde crosslinking. Note that crosslinking may result in monomeric hemoglobins that are crosslinked internally as well as polymeric hemoglobins that are crosslinked between tetramers. Thus the term crosslinked hemoglobin may refer to a single species of crosslinked hemoglobin, i.e. an intramolecularly crosslinked hemoglobin tetramer, or it may refer to a crosslinked hemoglobin solution that contains several different crosslinked hemoglobins (e.g. two tetramers linked together, three tetramers linked, etc.).

The crosslinking reactions can be terminated (or quenched) by the use of any suitable quenching reagents. Such quenching reagents include borohydrides and amino boranes (Geoghean et al., 1981, *Int. J. Peptide Protein Res.* 17: 345). Particularly suitable quenching or termination reagents are sodium cyanoborohydride and sodium borohydride.

Moreover, the crosslinked hemoglobin may be pyridoxylated or non-pyridoxylated. Suitable pyridoxylation techniques are discussed in Vandegriff, K. D.(1992) *Biotechnology and Genetic Engineering Reviews,* Volume 10: 404–453 M. P. Tombs, Editor, Intercept Ltd., Andover, England. Preferably, the crosslinked hemoglobin is non-pyridoxylated.

The instant invention is further directed to recombinantly produced hemoglobin that is crosslinked with aldehydes, particularly recombinantly produced hemoglobin that is crosslinked with aldehydes according to the methods of the instant invention discussed herein.

The crosslinked hemoglobin of the present invention, whether intramolecularly crosslinked, intermolecularly crosslinked or both, can be used for formulations useful for in vitro or in vivo applications. Such in vitro applications include, for example, the delivery of oxygen by compositions of the instant invention for the enhancement of cell growth in cell culture by maintaining oxygen levels in vitro (DiSorbo and Reeves, PCT publication WO 94/22482, herein incorporated by reference). Moreover, the crosslinked hemoglobin of the instant invention can be used to remove oxygen from solutions requiring the removal of oxygen (Bonaventura and Bonaventura, U.S. Pat. No. 4,343,715, incorporated herein by reference) and as reference standards for analytical assays and instrumentation (Chiang, U.S. Pat. No. 5,320,965, incorporated herein by reference) and other such in vitro applications known to those of skill in the art.

In a further embodiment, the crosslinked hemoglobin of the present invention can be formulated for use in therapeutic applications. Such formulations suitable for the crosslinked hemoglobin of the instant invention are described in Milne, et al., WO 95/14038 and Gerber et al., PCT/US95/10232, both herein incorporated by reference. Pharmaceutical compositions of the invention can be useful for, for example, subcutaneous, intravenous, or intramuscular injection, topical or oral administration, large volume parenteral solutions useful as blood substitutes, etc. Pharmaceutical compositions of the invention can be administered by any conventional means such as by oral or aerosol administration, by transdermal or mucus membrane adsorption, or by injection. The hemoglobins of the instant invention can also be incorporated into any suitable delivery vehicle for administration in either in vivo or in vitro uses, such as by encapsulation in liposomes, delivery either on or within particles, and the like.

The crosslinked hemoglobin of the present invention can be used in compositions useful as substitutes for red blood cells in any application that red blood cells are used. Such crosslinked hemoglobin of the instant invention formulated as red blood cell substitutes can be used for the treatment of hemorrhages, traumas and surgeries where blood volume is lost and either fluid volume or oxygen carrying capacity or both must be replaced. Moreover, because the crosslinked hemoglobin of the instant invention can be made pharmaceutically acceptable, the crosslinked hemoglobin of the instant invention can be used not only as blood substitutes that deliver oxygen but also as simple volume expanders that provide oncotic pressure due to the presence of the large hemoglobin protein molecule. In a further embodiment, the crosslinked hemoglobin of the instant invention can be used in situations where it is desirable to limit the extravasation of the hemoglobin-based blood substitute. The crosslinked hemoglobin of the present invention can be synthesized with a target oxygen affinity and cooperativity and a high molecular weight. Thus the crosslinked hemoglobin of the instant invention can act to transport oxygen as a red blood cell substitute, while reducing the adverse effects that can be associated with excessive extravasation.

A typical dose of the hemoglobins of the instant invention as an oxygen delivery agent can be from 1 mg to 5 grams or more of extracellular hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, and the particular purpose to be achieved according to the determination of the skilled artisan in the field.

Administration of crosslinked hemoglobin can occur for a period of seconds to hours depending on the purpose of the hemoglobin usage. For example, as a blood delivery vehicle, the usual time course of administration is as rapid as possible. Typical infusion rates for hemoglobin solutions as blood replacements can be from less than about 100 ml to over 3000 ml/hour.

In a further embodiment, the crosslinked hemoglobin of the instant invention can be used to treat anemia, both by providing additional oxygen carrying capacity in a patient that is suffering from anemia, and by stimulating hematopoiesis. When used to stimulate hematopoiesis, administration rates can be slow because the dosage of hemoglobin is much smaller than dosages that can be required to treat hemorrhage. Therefore the hemoglobin of the instant invention can be used for applications requiring administration to a patient of high volumes of hemoglobin as well as in situations where only a small volume of the crosslinked hemoglobin of the instant invention is administered. In addition, oxygen affinities and cooperativities that are particularly useful for the stimulation of hematopoiesis may be synthesized for these applications, as well as the other applications described herein, by modulation of the total and R-state hemoglobin, and/or the reaction parameters as described in the instant invention.

Because the distribution of the crosslinked hemoglobin in the vasculature is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation, any tissues that are suffering from oxygen starvation or are hypoxic, and the like. Additionally, any types of tissue ischemia can be treated using the hemoglobins of the instant invention. Such tissue ischemias include, for example, stroke, emerging stroke, transient ischemic attacks, myocardial stunning and hibernation, acute or unstable angina, emerging angina, infarct, and the like. Because of the broad distribution in the body, the hemoglobins of the instant invention can also be used to deliver drugs and for in vivo imaging.

The crosslinked hemoglobin of the instant invention can also be used as replacement for blood that is removed during surgical procedures where the patient's blood is removed and saved for reinfusion at the end of surgery or during recovery (acute normovolemic hemodilution or hemoaugmentation). In addition, the crosslinked hemoglobin of the instant invention can be used to increase the amount of blood that may be predonated prior to surgery, by acting to replace some of the oxygen carrying capacity that is donated.

Under normal physiological conditions, nitric oxide is not produced in excess amounts. However, certain disease states are associated with excess nitric oxide production. Such conditions include septic shock and hypotension. In these cases, the crosslinked hemoglobin of the present invention can be used to remove excess nitric oxide.

The following examples are provided by way of describing specific embodiments of the present invention without intending to limit the scope of the invention in any way.

EXAMPLE 1

Preparation of Hemoglobin for Crosslinking

Recombinant hemoglobin (rHb1.1) was expressed, prepared and purified as described in PCT publication number WO 95/14038, filed Nov. 15, 1994, entitled "Purification of Hemoglobin" herein incorporated by reference in its entirety. Hemoglobin (39 g of recombinant hemoglobin in 239 ml of standard buffer-150 mM NaCl, 5 mM sodium phosphate, pH 7.4; 160 mg/ml) was deoxygenated in a 1 L round bottom flask by purging for 2–5 hours with humidified nitrogen on a Brinkmann ROTOVAP RE111 (Brinkmann, Inc., Cuntiague Road, Westbury, N.Y.).

EXAMPLE 2

Glutaraldehyde Crosslinking

Following deoxygenation, the solution was capped with a white rubber septum and glutaraldehyde (25% aqueous solution, Sigma Chemical Company, St. Louis, Mo.) was then added slowly while stirring. The solution was incubated for 16 hours at 4° C. while stirring. Next, sodium cyanoborohydride (3.04 g in 25 ml of deoxygenated buffer—10:1 mol NaCNBH$_3$:mol glutaraldehyde) was added dropwise while stirring at room temperature. The solution was stirred an additional 5.5 hours at room temperature then diafiltered against 10 volumes of standard buffer. Following diafiltration the solution was divided into aliquots and stored at −80° C.

EXAMPLE 3

Preparation of Glycoaldehyde Crosslinked Hemoglobin

Hemoglobin was expressed, prepared and purified as described in co-owned PCT publication number, WO 95/13034, filed Nov. 14, 1994, entitled "Purification of Hemoglobin." 1857 mg of recombinant hemoglobin in 12.4 ml standard buffer (150 mM NaCl, 5 mM sodium phosphate, pH 7.4) (approximately 150 mg/ml solution) was deoxygenated in a 100 ml round bottom flask by 25 purging for 4 hours with humidified nitrogen on a ROTOVAP cooled to 10° C. During the deoxygenation, a 10% solution of glycolaldehyde (Sigma Chemical Company, St. Louis, Mo.) was prepared in standard buffer and stored on ice. After deoxygenation of the hemoglobin, 3 ml of glycolaldehyde were deoxygenated by evacuating the container then purging with nitrogen gas. All equipment and solutions were then placed in a glove bag which was brought to approximately 90 ppm oxygen as measured by a MOCON apparatus (Mocon, Inc., Minneapolis, Minn.). 1.4 ml aliquots of hemoglobin were placed in 3 ml glass vials and glycolaldehyde was added at ratios of 8, 10, 12, 14, 16, 18, 20 and 22 moles of glycolaldehyde per mole of hemoglobin. The vials were capped with gray rubber septa. The solutions were incubated with stirring overnight at 4° C. The next day, a 250 µg/µl solution of sodium cyanoborohydride in standard buffer was prepared, degassed and flushed with nitrogen gas. All supplies and equipment were then again placed in a glove bag which was then brought to approximately 90 ppm oxygen. The vials were unstoppered, and cyanoborohydride was added (10:1 moles of cyanoborohydride to moles of glycolaldehyde) with stirring at room temperature. The vials were re-capped and incubated at 25° C. for 3 hours. After 3 hours, 0.5 ml aliquots were withdrawn from each vial and diluted to 2.5 mls with standard buffer. The solutions were then desalted in Pharmacia PD-10 columns using the manufacturer's recommended procedure. The remainders of each of the solutions were stored without further processing at −80° C.

EXAMPLE 4

Measurement of Oxygen Affinity and Cooperativity

Oxygen equilibrium curves were measured according to the method described in Hoffman et al. (Hoffman, S J., Looker, D. L., Roehrich, J. M., Cozart, P. E., Durfee, S. L., Tedesco, J. L. and Stetler, G. L. (1990) *Proc. Natl. Acad. Sci. USA* 87:8521–8525) except that all determinations were made using 50 mM HEPES/0.1 M NaCl at 37° C. $P_{50}$ values and $n_{max}$ values were then derived from the oxygen equilibrium curves as described by Hoffman et al., ibid.

EXAMPLE 5

Determination of Molecular Weight Distribution of Crosslinked Hemoglobin

The molecular weight distribution of the crosslinked hemoglobins prepared according to the methods of the instant invention was determined using high performance size exclusion chromatography (HPSEC). Hemoglobin solutions were diluted to approximately 10 mg/ml concentrations in 5 mM sodium phosphate, 150 mM NaCl, pH 7.8. Aliquots (25 µl) were chromatographically separated using a Pharmacia SUPEROSE 12 and SUPEROSE 6 (Pharmacia Biotech, Uppsala, Sweden) size exclusion columns connected in series. The columns were eluted with the same buffer as the dilution buffer at a flow rate of 0.5 ml/min. Absorbance was monitored at 215 nm. Molecular weights were determined by comparing to a set of gel filtration standards (Sigma Chemical Co., St. Louis, Mo.). The percent of protein in each molecular weight range was determined using integration software provided with the HP1090 HPLC system (Hewlett Packard Corp., Wilmington, Del.).

EXAMPLE 6

Hemin Dissociation Rate Measurement

Time courses for the dissociation of hemin were measured using the H64Y/V68F apomyoglobin reagent developed by Hargrove et al., (Hargrove, M. S., Singleton, E. W., Quillin, M. L., Mathews, A. J., Ortiz, L. A., Phillips, G. N., Jr., & Olson, J. S. (1994) *J. Biol. Chem.* 269, 4207–4214). The reactions were measured at 37° C. in 0.15 M $KPO_4$/0.45M sucrose at either pH 5.0 (sodium acetate) or pH 7 (potassium phosphate). The reactions contained ~6.0 µM (unless otherwise specified) methemoglobin in the presence of excess H64Y/V68F apomyoglobin, generally 12.0–24.0 µM. The H64Y/V68F myoglobin heme loss reagent has an unusual absorption spectra giving rise to a green color. The reaction can be described by:

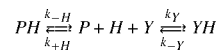

where P represents the heme containing globin of interest, H is equal to heme, and Y is the H64Y/V68F mutant apomyoglobin. When [P] and/or [Y] are >>[H], the d[H] dt~0, and the rate of hemin dissociation, $k_{-H}$, is given by:

$$\frac{k_{-H} + k_{-Y}\left(\frac{k_H[P]}{k_Y[Y]}\right)}{1 - \frac{k_H[P]}{k_Y[Y]}}$$

which reduces to $r_{obs}=k_{-H}$ when [Y]>>[P] (Hargrove, M. S., Singleton, E. W., Quillin, M. L., Mathews, A. J., Ortiz, L. A., Phillips, G. N., Jr., & Olson, J. S. (1994) *J. Biol. Chem.* 269, 4207–4214).

The total reaction volumes were 800 µL and measured in a 1.0 ml cuvette with a 1.0 cm path length. A six cell Shimadzu 2101 UV-Vis spectrophotometer (Shimadzu Scientific Instruments, Columbia, Md.) connected to a CPS-260 temperature controller was used to collected the absorbance changes at the specified time intervals. The hemoglobin of interest was first oxidized with ferricyanide. One grain of ferricyanide was added to about 50 µL of 1 mM oxy- or carbonmonoxyhemoglobin. The protein solution was then run down a G25 SEPHADEX (Sigma Chemical Company, St. Louis, Mo.) column equilibrated in 10.0 mM potassium phosphate pH 7 at room temperature. The buffer and H64Y/V68F apomyoglobin reagent were equilibrated at the specified temperature in the spectrophotometer prior to the addition of the ferric protein of interest. Time courses were fitted to single or double exponential expressions using the IGOR Pro analysis program (Wavemetrics, Inc., Lake Oswego, Oreg.).

Hemoglobin time courses were biphasic with hemin loss from the alpha and beta subunits showing equal absorbance changes. The fast phase of hemin loss is due to hemin loss from the beta subunits and the slow phase to hemin loss from alpha subunits. Hemoglobin time courses were fitted to a two exponential expression with equal amplitudes. Occasionally, the time courses were fit to a three exponential expression with the third phase representing slow absorbance drift caused by protein denaturation.

EXAMPLE 7

Methemoglobin Determination

Methemoglobin is hemoglobin wherein one or more of the irons of the heme prosthetic groups are in the $Fe^{+3}$ (ferric) oxidation state. The measurement technique for methemoglobin described herein measures the oxidation state of individual heme irons. Thus, the reported percentage of methemoglobin reflects the percentage of hemes that are oxidized in the hemoglobin sample.

Five microliters of hemoglobin solutions were added to 500 µl of 0.1 M Tris, pH 8.0. 200 µl of the diluted hemoglobin solution was then added to 2.8 ml of 0.1 M Tris, pH 8.0 in a 4.5 ml cuvette for a final dilution of 1:1500. The oxygenated sample (Hb) was then analyzed by spectrophotometry in a Hewlett-Packard model HP 8452A spectrophotometer. Absorbances at 436, 425, 420, 404, 400 nm were collected and stored in a data storage system. The cuvette was then removed from the spectrophotometer and sparged with carbon monoxide two times for 15 seconds each time. The cuvette was inverted 5 times between each sparge. The sample was then re-inserted into the spectrophotometer, and a second set of spectra were collected that corresponded to carbonmonoxy hemoglobin (HbCO). The cuvette was then again removed from the spectrophotometer and 30 $\mu$l of 0.1M KCN in 0.1 M Tris, pH 8.0 was added to the sample. The sample was then inverted three times, allowed to incubate for 5 minutes, and re-inserted into the spectrophotometer for a final spectrophotometric analysis (HbCN). The percent methemoglobin was then calculated as follows:

$$\% \; Met \; Hb = \frac{[A_{425}^{HbCN} - A_{404}^{HbCN}] - [A_{425}^{Hb} - A_{404}^{Hb}]}{[A_{420}^{HbCO} - A_{436}^{HbCO}] - [A_{420}^{Hb} - A_{436}^{Hb}] + [A_{425}^{HbCN} - A_{404}^{HbCN}] - [A_{425}^{Hb} - A_{404}^{Hb}]} * 100$$

where A=the absorbance at the susbcripted wavelength for the superscripted hemoglobin species.

EXAMPLE 8

Characterization of Glutaraldehyde Crosslinked Hemoglobin

The physical characterization data of a glutaraldehyde-crosslinked recombinant hemoglobin prepared as described in Example 1 and 2 are shown in Table 3.

Methemoglobin was measured as described in Example 7. Following crosslinking and purification the metHb levels were relatively low. The functionality was determined as described in Example 4. The functionality of the hemoglobin was also relatively unchanged by the crosslinking procedure with the $P_{50}$ remaining at 32.72. Although the $n_{max}$ decreased to 1.31, this change also occurred in the monomeric fraction of the glutaraldehyde-crosslinked hemoglobin suggesting that intramolecular crosslinks occurred prior to crosslinking higher order species. The hemin dissociation rates was determined according to the methods described in Example 6. The hemin dissociation rates were only slightly affected by the glutaraldehyde-crosslinking. The dissociation rate for the beta-globin increased 56% from 2.5 hr$^{-1}$ for non-crosslinked rHb1.1 to 3.9 hr$^{-1}$ for the crosslinked species. Likewise, the dissociation rate for the dialphaglobin chains (two alpha chains genetically fused, described in PCT publication WO 90/13645, herein incorporated by reference) increased 25% from 0.4 hr$^{-1}$ for non-crosslinked rHb1.1 to 0.5 hr$^{-1}$ for the crosslinked hemoglobin.

The molecular weight distribution of the crosslinked species was determined using HPSEC as described in Example 5. The purified crosslinked hemoglobin contained a broad distribution of molecular weights (~150–3000 kD) with the molecular weight of the main peak centered at ~430 kD. There was also a small quantity of monomeric (~64 kD) and dimeric (~128 kD) hemoglobin. The monomeric hemoglobin constituted ~0.6% of the purified product and the dimer constituted ~1.1% of the hemoglobin. The quantity of hemoglobin which eluted with a molecular weight equivalent to that of trimeric hemoglobin (194 kD) was determined by the total absorbance between 150–214 kD. The other estimated molecular weight distributions shown in Table 3 were determined in a similar manner using the appropriate molecular weight ranges. The average diameter of the crosslinked hemoglobins was determined using dynamic light scattering using a Nicomp C370 instrument (Particle Sizing Systems, Santa Barbara, Calif.), and shown to be ~17.8 nm. Based on X-ray crystallography the diameter of this recombinant hemoglobin is 4.9 nm, suggesting that the crosslinked hemoglobins ranged from ~2–5 hemoglobin molecules across with an average of ~34 hemoglobins.

Endotoxins were determined using the Limulus Ameobocyte Lysate assay used according to the manufacturers instructions (Cape Cod Associates, Falmouth, Mass.).

TABLE 3

| Assay | Starting Material | Final Material |
|---|---|---|
| % methemoglobin | 2.7 | 5.9 |
| $P_{50}$ (mmHg) | 31.6 | 32.7 |
| $n_{max}$ | 2.4 | 1.3 |
| Molecular Weight Distribution | Monomer 97.7% | Monomer 0.6% |
|  | Dimer 0.3% | Dimer 1.1% |
|  |  | Trimer (150–214 kD) 6.9% |
|  |  | 214–800 kD 78.6% |
|  |  | 800–3000 kD 12.8% |
|  |  | (Peak MW = 430 kD) |
| Average Diameter | ~6 nm | 17.8 ± 7.6 nm |
| Hemin Dissociation Rates (hr$^{-1}$) | $k_{rHb1.1\text{-beta}} = 2.5$ | $k_{beta} = 3.9$ |
|  | $k_{rHb1.1\text{-di-alpha}} = 0.4$ | $k_{di\text{-alpha}} = 0.5$ |

EXAMPLE 9

Oxygen Affinity Versus Residual Oxyhemoglobin Content—Glutaraldehyde Crosslinking Hemoglobin was prepared and crosslinked as described in Examples 1 and 2, except that the procedure was performed in room air with 100% oxyhemoglobin concentration, 50 mg/ml hemoglobin concentration, 50 mg/ml hemoglobin deoxygenated to 0.4–0.5% oxyhemoglobin concentration. The material was analyzed for functionality ($P_{50}$ and $n_{max}$) as described in Example 4. Results are presented in Table 4.

TABLE 4

|  | 0.4–0.5% Oxyhemoglobin | 100% Oxyhemoglobin |
|---|---|---|
| $P_{50}$ | 46 | 9.4 |
| $n_{max}$ | 1.27 | 1.01 |

EXAMPLE 10

Oxygen Affinity and Cooperativity Versus Hemoglobin Concentration—Glutaraldehyde Crosslinking Crosslinked hemoglobin was prepared as described in Examples 1 and 2. Four different hemoglobin concentrations (48, 96, 134 and 160 mg/ml) of the uncrosslinked material were prepared and crosslinked with 13, 11, 9 and 8 moles of glutaraldehyde per mole of hemoglobin respectively. Glutaraldehyde was diluted to 0.2 mmol/ml prior to addition to the hemoglobin solutions. All hemoglobin concentrations were prepared in 2 ml aliquots prior to crosslinking, except for the 160 mg/ml concentration. This high concentration was prepared in a 200 ml aliquot and crosslinked with undiluted glutaraldehyde. There were no differences in reactions performed with diluted versus undiluted glutaraldehyde, or low versus high volume reactions. Note that the concentration of glutaraldehyde was adjusted merely to provide similar chromatographic profiles after crosslinking (i.e. the same degree of crosslinking). All hemoglobin solutions and glutaraldehyde solutions were deoxygenated to less than 0.1% oxyhemoglobin prior to crosslinking, and all reactions were performed in inert environments. Crosslinking reactions were allowed to continue for 16 hours and quenched with cyanoborohydride as described in Example 2.

Oxygen affinities ($P_{50}$'s) and cooperativities ($n_{max}$) were determined according to Example 4 and are listed below in Table 5. Note that as hemoglobin concentration increased, $P_{50}$ decreased while $n_{max}$ increased in a regular manner.

EXAMPLE 12

Effect of Temperature on Functionality—4° C. VS 25° C.

For each reaction, an aliquot (6 ml in a 50 ml round bottomed flask) of recombinant hemoglobin was deoxygenated as previously described.

Glutaraldehyde was added as a single addition in an 8:1 molar ratio of glutaraldehyde to hemoglobin. The mixture was allowed to react with stirring at either 4° C. or 25° C. as indicated in Table 7. Aliquots (0.5 ml) were removed at the indicated time periods and quenched with sodium borohydride in 0.1N NaOH. Each aliquot was then buffer exchanged into 150 mM NaCl, 5 mM Sodium phosphate, pH 7.8 using PD-10 desalting columns (Pharmacia Biotech, Uppsala, Sweden). Molecular weight distributions were obtained as described in Example 5. Protein functionality of the polymer mixtures were determined as described in Example 4.

TABLE 7

Hemoglobin as a Function of Temperature and Reaction Time

| | 4° C. (154 mg/ml) | | | | | 25° C. (165 mg/ml) | | | | |
|---|---|---|---|---|---|---|---|---|---|---|
| | 0 min | 10 min | 30 min | 60 min | 120 min | 0 min | 1 min | 3 min | 5 min | 10 min |
| 65 kDa | 97.7 | 38.9 | 24.5 | 27.7 | 32.8 | 95.7 | 47.5 | 32.0 | 31.6 | 33.9 |
| 128 kDa | 2.2 | 19.9 | 13.7 | 15.4 | 17.8 | 4.3 | 20.9 | 17.5 | 17.4 | 18.5 |
| 190 kDa | | 13.4 | 10.0 | 11.2 | 12.7 | | 11.6 | 12.2 | 12.2 | 12.9 |
| >230 kDa | | 27.8 | 51.6 | 45.6 | 34.9 | | 20.0 | 38.2 | 38.8 | 34.6 |
| $P_{50}$ | 29.2 | 28.3 | 29.4 | 28.4 | 27.8 | 29.9 | 30.1 | 30.3 | 28.4 | 29.2 |
| $n_{max}$ | 2.13 | 1.69 | 1.54 | 1.43 | 1.41 | 2.22 | 1.75 | 1.59 | 1.51 | 1.49 |

TABLE 5

| Hemoglobin Concentration (mg/ml) | Glutaraldehyde: Hemoglobin ratio (mol:mol) | $P_{50}$ | $n_{max}$ |
|---|---|---|---|
| 48 | 13:1 | 47 | 1.27 |
| 96 | 11:1 | 45 | 1.30 |
| 134 | 9:1 | 42 | 1.35 |
| 160 | 8:1 | 32 | 1.43 |

EXAMPLE 11

Oxygen Affinity Versus Residual Oxyhemoglobin Content—Glutaraldehyde Crosslinking Hemoglobin was prepared and crosslinked as described in Examples 1 and 2, except that the procedure was performed in room air with 100% oxyhemoglobin concentration, 125 mg/ml hemoglobin concentration and 50 mg/ml hemoglobin concentration. The material was analyzed for functionality ($P_{50}$ and $n_{max}$) as described above. Results are listed in Table 6.

TABLE 6

| | 50 mg/ml total hemoglobin | 125 mg/ml total hemoglobin |
|---|---|---|
| $P_{50}$ | 9.4 | 11.9 |
| $n_{max}$ | 1.01 | 1.12 |

EXAMPLE 13

Effect of Protein Concentration

For each reaction an aliquot (6 ml in a 50 ml round bottom flask) of recombinant hemoglobin (51 mg/ml or 154 mg/ml in 5 mM Sodium phosphate, pH 7.1) was deoxygenated as described previously. Glutaraldehyde was added as a single addition as either a 12.5:1 (51 mg/ml) or 8:1 (154 mg/ml) molar ratios glutaraldehyde:rHb1.1 and allowed to react with stirring at 4° C. for the indicated time. Aliquots (0.5 ml) were removed at the indicated time periods and quenched with sodium borohydride in 0.1N NaOH. Each aliquot was then buffer exchanged into 150 mM NaCl, 5 mM Sodium phosphate, pH 7.8 using PD-10 desalting columns (Pharmacia Biotech, Uppsala, Sweden). Molecular weight distributions were then determined as described in Example 5. Protein functionality of the polymer mixtures were determined as described in Example 4.

TABLE 8

| | Reaction Time | | | | | |
|---|---|---|---|---|---|---|
| | 51 mg/ml rHb1.1 — 12.5:1 ratio mol glutaraldehyde:mol rHb1.1 | | | 154 mg/ml rHb1.1 — 8:1 ratio mol glutaraldehyde:mol rHb1.1 | | |
| Functionality | 30 minutes | 60 minutes | 120 minutes | 30 minutes | 60 minutes | 120 minutes |
| $P_{50}$ | 26.6 | 28.3 | 30.6 | 29.4 | 28.4 | 27.8 |
| $n_{max}$ | 1.55 | 1.36 | 1.24 | 1.54 | 1.43 | 1.41 |

EXAMPLE 14

Effect of NaCl Concentration on Protein Functionality

For each reaction an aliquot (6 ml in a 50 ml round bottom flask) of recombinant hemoglobin (154 mg/ml in 5 mM Na-phosphate, pH 7.1±150 mM NaCl) was deoxygenated as described previously. Glutaraldehyde was added as a single addition of 8:1 molar ratio glutaraldehyde:rHb1.1 and allowed to react with stirring at 4° C. for the indicated time. Aliquots (0.5 ml) were removed at the indicated time periods and quenched with sodium borohydride in 0.1N NaOH. Each aliquot was then buffer exchanged into 150 mM NaCl, 5 mM Na-phosphate, pH 7.8 using PD-10 desalting columns (Pharmacia Biotech, Uppsala, Sweden). Molecular weight distributions were then determined as described in Example 5. Protein functionality of the polymer mixtures was determined by oxygen equilibrium curves. Oxygen equilibrium curves were measured according to the method described in Hoffman et al. (Hoffman, S. J., Looker, D. L., Roehrich, J. M., Cozart, P. E., Durfee, S. L., Tedesco, J. L. and Stetler, G. L. (1990) *Proc. Natl. Acad. Sci. USA* 87:8521–8525) except that all determinations were made using 50 mM HEPES/0.1 M NaCl at 37° C. $P_{50}$ values and $n_{max}$ values were then derived from the oxygen equilibrium curves.

TABLE 9

| | Reaction Time | | | | | |
| --- | --- | --- | --- | --- | --- | --- |
| | 0 mM NaCl | | | 150 mM NaCl | | |
| functionality | 30 minutes | 60 minutes | 120 minutes | 30 minutes | 60 minutes | 120 minutes |
| $P_{50}$ | 29.4 | 28.4 | 27.8 | 29.34 | 29.47 | 27.36 |
| $n_{max}$ | 1.54 | 1.43 | 1.41 | 1.57 | 1.53 | 1.43 |

EXAMPLE 15

Effect of pH on Crosslinking Reaction—pH 7 Vs pH 9

For each reaction an aliquot (6 ml in a 50 ml round bottom flask) of recombinant hemoglobin (154 mg/ml in 5 mM Na-phosphate, pH 7.1 or 155 mg/ml in 5 mM sodium borate, pH 9.0) was deoxygenated as described previously. Glutaraldehyde was added as a single addition of 8:1 molar ratio glutaraldehyde:rHb1.1 and allowed to react with stirring at 4° C. for the indicated time. Aliquots (0.5 ml) were removed at the indicated time periods and quenched with sodium borohydride in 0.1N NaOH. Each aliquot was then buffer exchanged into 150 mM NaCl, 5 mM Na-phosphate, pH 7.8 using PD-10 desalting columns (Pharmacia Biotech, Uppsala, Sweden). Protein functionality of the polymer mixtures was determined as described in Example 4, molecular weight distributions were determined as described in Example 5.

TABLE 10

| | Reaction Time | | | | | |
| --- | --- | --- | --- | --- | --- | --- |
| | pH 7.1 | | | pH 9.0 | | |
| Functionality | 0 minutes | 30 minutes | 60 minutes | 0 minutes | 30 minutes | 60 minutes |
| $P_{50}$ | 29.2 | 29.4 | 28.4 | 28.5 | 28.4 | 30.3 |
| $n_{max}$ | 2.13 | 1.54 | 1.43 | 2.09 | 1.48 | 1.30 |

EXAMPLE 16

Effect of Rate of Addition of Crosslinking Agent on Functionality

For each reaction an aliquot (6 ml or 5 ml in a 50 ml round bottom flask) of recombinant hemoglobin (154 mg/ml in 5 mM Na-phosphate, pH 7.1) was deoxygenated as described previously. Glutaraldehyde was added as a single addition of 8:1 molar ratio glutaraldehyde:rHb1.1(the ratio at the end of the experiment) and allowed to react with stirring at 4° C. for the indicated time. For the experiment with the single glutaraldehyde addition no other adjustments were made to the solution. For the second reaction, following addition of glutaraldehyde another 2.5 ml of deoxygenated rHb1.1 in the same buffer was added over a 15 minute period using a syringe pump. Aliquots (0.5 ml) were removed at the indicated time periods and quenched with sodium borohydride in 0.1N NaOH. Each aliquot was then buffer exchanged into 150 mM NaCl, 5 mM Na-phosphate, pH 7.8 using PD-10 desalting columns (Pharmacia Biotech, Uppsala, Sweden). Molecular weight distributions were then determined as described in Example 5, while functionality was determined as described in Example 4.

TABLE 11

| | Protein distribution represented as % of total crosslinked protein Reaction Time | | | | | | | |
| --- | --- | --- | --- | --- | --- | --- | --- | --- |
| Molecular Weight | Single addition of glutaraldehyde | | | | Single addition of glutaraldehyde + slow addition of rHb1.1. | | | |
| (kDa) | 0 min | 10 min | 30 min | 60 min | 0 min | 15 min | 30 min | 60 min |
| 65 | 97.7 | 38.9 | 24.5 | 27.7 | 97.9 | 53.3 | 34.9 | 38.2 |
| 128 | 2.2 | 19.9 | 13.7 | 15.4 | 2.1 | 21.5 | 18.5 | 19.7 |
| 190 | | 13.4 | 10.0 | 11.2 | | 11.4 | 12.8 | 13.4 |
| >230 | | 27.8 | 51.6 | 45.6 | | 13.8 | 33.8 | 28.8 |
| $P_{50}$ | 29.2 | 28.3 | 29.4 | 28.4 | 30.4 | 28.0 | 29.0 | 29.0 |
| $n_{max}$ | 2.13 | 1.69 | 1.54 | 1.43 | 2.27 | 1.84 | 1.67 | 1.59 |

What is claimed is:

1. A method for preparing a crosslinked hemoglobin solution having a target Hill coefficient comprising:
 (a) obtaining a deoxygenated hemoglobin solution;
 (b) controlling at least one Hill coefficient-affecting parameter during chemical treatment of said deoxygenated hemoglobin solution, to produce said crosslinked hemoglobin solution having the target Hill coefficient.

2. The method of claim 1, wherein said target Hill coefficient is in the range from about 1.0 to about 3.0.

3. The method of claim 1, wherein said crosslinked hemoglobin solution contains intramolecularly crosslinked hemoglobin.

4. The method of claim 1, wherein said crosslinked hemoglobin solution contains a mixture of intra- and intermolecularly crosslinked hemoglobin.

5. The method of claim 1 wherein said chemical treatment is with a crosslinking reagent selected from the group consisting of a bis-imidodiester, a bis-succinimidyl ester and an aldehyde.

6. The method of claim 5, wherein said aldehyde is glutaraldehyde.

7. The method of claim 6, wherein hemoglobin and glutaraldehyde are mixed simultaneously.

8. The method of claim 1, wherein said parameter is time of treatment.

9. The method of claim 8, wherein time of treatment is up to about 120 minutes.

10. The method of claim 9, wherein said time of treatment is less than about 10 minutes.

11. The method of claim 10, wherein said time of treatment is less than about 1 minute.

12. The method of claim 1, wherein said parameter is pH.

13. The method of claim 12, wherein the pH is between about 6.5 and about 7.5.

14. The method of claim 1, wherein said parameter is temperature.

15. The method of claim 14, wherein said temperature is up to about 80° C.

16. The method of claim 1, wherein said parameter comprises adjustment of the rate of addition of hemoglobin.

17. The method of claim 1, wherein said hemoglobin is recombinant hemoglobin.

18. The method of claim 1, wherein said Hill coefficient-affecting parameter is the molar ratio of a crosslinking reagent to hemoglobin.

19. The method of claim 18, wherein said molar ratio is from about 8:1 to about 12.5:1 of crosslinking reagent to hemoglobin.

20. The method of claim 19, wherein said molar ratio is about 8:1 of crosslinking reagent to hemoglobin.

21. The method of claim 19, wherein said molar ratio is about 12.5:1 of crosslinking reagent to hemoglobin.

* * * * *